(12) United States Patent
Hilt et al.

(10) Patent No.: US 12,427,725 B2
(45) Date of Patent: Sep. 30, 2025

(54) ENERGY MECHANISM ASSEMBLIES AND METHODS OF PROVIDING ENERGY TO AN ITEM

(71) Applicant: Kimberly-Clark Worldwide, Inc., Neenah, WI (US)

(72) Inventors: Ronald A. Hilt, Oshkosh, WI (US); Kelly D. Farmer, Arden, NC (US); Craig R. Roble, Rothchild, WI (US); Matthew D. Opsteen, Menasha, WI (US); Jason A. Verboomen, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 93 days.

(21) Appl. No.: 18/251,996

(22) PCT Filed: Dec. 17, 2020

(86) PCT No.: PCT/US2020/065512
§ 371 (c)(1),
(2) Date: May 5, 2023

(87) PCT Pub. No.: WO2022/132149
PCT Pub. Date: Jun. 23, 2022

(65) Prior Publication Data
US 2023/0405939 A1 Dec. 21, 2023

(51) Int. Cl.
*B29C 65/08* (2006.01)
*B29C 65/00* (2006.01)
(Continued)

(52) U.S. Cl.
CPC ........ *B29C 65/085* (2013.01); *B29C 65/7885* (2013.01); *B29C 65/7894* (2013.01);
(Continued)

(58) Field of Classification Search
CPC .................................................. B29C 65/085
See application file for complete search history.

(56) References Cited

U.S. PATENT DOCUMENTS

| 4,190,010 A | 2/1980 | Bibby |
| 4,457,243 A | 7/1984 | Bowditch |
(Continued)

FOREIGN PATENT DOCUMENTS

| EA | 021012 B1 | 3/2015 |
| EP | 0320989 A2 | 6/1989 |
(Continued)

OTHER PUBLICATIONS

Altrasonic, "Ultrasonic Bonding of Nonwovens, Films and Textiles". Altrasonic.com, Apr. 28, 2015, http://www.altrasonic.com/Ultrasonic-Bonding-Of-Nonwovens-Films-And-Textiles_n28.

*Primary Examiner* — Jeffry H Aftergut
(74) *Attorney, Agent, or Firm* — KIMBERLY-CLARK WORLDWIDE, INC.

(57) ABSTRACT

Energy mechanism assemblies and methods of operating such assemblies are described. One method of providing energy to an item may comprise positioning an item proximate an energy mechanism assembly comprising a first and second energy mechanism and a translation system configured to move the second mechanism along between a first position and a second position along a first axis and a second axis, positioning the item between the first and second mechanisms, moving the second mechanism from the first position to the second position, moving the second mechanism along the second axis for a first length while the second mechanism is in contact with the item; and providing energy to the item at least while the second mechanism contacts the item.

17 Claims, 7 Drawing Sheets

(51) Int. Cl.
*B29C 65/78* (2006.01)
*B29L 31/48* (2006.01)

(52) U.S. Cl.
CPC .... *B29C 66/1122* (2013.01); *B29C 66/73921* (2013.01); *B29C 66/83221* (2013.01); *B29C 66/83511* (2013.01); *B29L 2031/4878* (2013.01)

(56) References Cited

U.S. PATENT DOCUMENTS

| | | |
|---|---|---|
| 4,670,073 A | 6/1987 | Langley |
| 4,938,817 A | 7/1990 | Langley |
| 5,238,170 A | 8/1993 | Nuss |
| 5,246,433 A | 9/1993 | Hasse et al. |
| 5,568,779 A | 10/1996 | Wong |
| 5,569,234 A | 10/1996 | Buell et al. |
| 5,643,396 A | 7/1997 | Rajala et al. |
| 5,772,825 A | 6/1998 | Schmitz |
| 5,817,199 A | 10/1998 | Brennecke et al. |
| 6,113,717 A | 9/2000 | Vogt et al. |
| 6,368,437 B1 | 4/2002 | Ziegelhoffer et al. |
| 6,450,393 B1 | 9/2002 | Doumanidis et al. |
| 6,454,752 B1 | 9/2002 | Huang et al. |
| 6,537,401 B2 | 3/2003 | Couillard et al. |
| 6,579,275 B1 | 6/2003 | Pozniak et al. |
| 7,162,749 B2 | 1/2007 | Carbone, II et al. |
| 7,722,591 B2 | 5/2010 | Bäck |
| 7,887,656 B2 | 2/2011 | Yamamoto |
| 7,959,619 B2 | 6/2011 | Cartier et al. |
| 8,029,631 B2 | 10/2011 | Cartier et al. |
| 8,197,458 B2 | 6/2012 | Bäck |
| 8,449,519 B2 | 5/2013 | Een et al. |
| 8,662,133 B2 | 3/2014 | Ninomiya et al. |
| 8,776,856 B2 * | 7/2014 | Yamamoto .......... B29C 66/0062 156/580.2 |
| 9,289,329 B1 | 3/2016 | Schaap |
| 9,517,169 B2 | 12/2016 | Nakakado |
| 9,655,786 B2 | 5/2017 | Piantoni et al. |
| 9,993,370 B2 | 6/2018 | Fujita et al. |
| 11,351,737 B2 | 6/2022 | Lohoff et al. |
| 2002/0005257 A1 | 1/2002 | Tomsovic et al. |
| 2003/0000620 A1 | 1/2003 | Herrin et al. |
| 2003/0075258 A1 | 4/2003 | Zhang et al. |
| 2003/0120252 A1 | 6/2003 | Franke et al. |
| 2003/0126673 A1 | 7/2003 | Yardley |
| 2004/0102757 A1 | 5/2004 | Olson |
| 2005/0133144 A1 | 6/2005 | You et al. |
| 2005/0230026 A1 | 10/2005 | Kramer |
| 2006/0165939 A1 | 7/2006 | Hottner |
| 2007/0251643 A1 | 11/2007 | Umebayashi et al. |
| 2008/0114325 A1 | 5/2008 | Edwall et al. |
| 2009/0061151 A1 | 3/2009 | LaFond et al. |
| 2009/0088713 A1 | 4/2009 | Norrby |
| 2009/0204093 A1 | 8/2009 | Vasic et al. |
| 2010/0063468 A1 | 3/2010 | Lehto et al. |
| 2010/0268183 A1 | 10/2010 | Een et al. |
| 2011/0173796 A1 | 7/2011 | Lavon et al. |
| 2011/0174432 A1 | 7/2011 | Lavon et al. |
| 2011/0297294 A1 | 12/2011 | McCabe |
| 2012/0065043 A1 | 3/2012 | Lam et al. |

FOREIGN PATENT DOCUMENTS

| | | | |
|---|---|---|---|
| EP | 1197252 A1 * | 4/2002 | |
| EP | 2100575 B1 | 11/2014 | |
| EP | 3092994 A1 * | 11/2016 | |
| EP | 2886089 B1 | 10/2021 | |
| GB | 2016537 A | 9/1979 | |
| GB | 2071564 A | 9/1981 | |
| GB | 2134036 A | 8/1984 | |
| JP | 1994307660 A | 11/1994 | |
| JP | 2004-248825 A * | 9/2004 | |
| JP | 2004298413 A | 10/2004 | |
| JP | 2012120775 A | 6/2012 | |
| JP | 5089821 B1 | 12/2012 | |
| JP | 2013501619 A | 1/2013 | |
| JP | 2015136820 A | 7/2015 | |
| RU | 2402249 C2 | 10/2010 | |
| WO | 2006087224 A1 | 8/2006 | |
| WO | 2010110708 A1 | 9/2010 | |
| WO | 2015104879 A1 | 7/2015 | |
| WO | 2016112925 A1 | 7/2016 | |
| WO | 2016130049 A1 | 8/2016 | |
| WO | WO-2019125264 A1 * | 6/2019 | ....... A61F 13/15699 |
| WO | WO-2019/212767 A1 * | 11/2019 | |

* cited by examiner

ENERGY MECHANISM ASSEMBLIES AND METHODS OF PROVIDING ENERGY TO AN ITEM

TECHNICAL FIELD

The present disclosure relates to an energy mechanism assemblies and methods of providing energy to an item. More specifically, the present disclosure relates to an ultrasonic bonding apparatus and methods of utilizing the same.

BACKGROUND OF THE DISCLOSURE

Various manufacturing equipment and processes employ a variety of techniques to transfer energy to an item, which can be for accomplishing different tasks. Energy transfer mechanisms can include apparatuses configured for cutting, sealing, embossing, pressure bonding, and ultrasonic bonding, to name a few. In the manufacturing of some absorbent articles, ultrasonic bonding equipment is one energy transfer apparatus that can be utilized for providing an ultrasonic bond on one or more components of an absorbent article. As one example, some absorbent articles include side panels having a side seam bond that can be formed by transferring ultrasonic energy from respective components of an ultrasonic bonding apparatus commonly referred to as an anvil and an ultrasonic horn across the web of material forming the side panels.

While current ultrasonic bonding equipment can provide sufficient bonds in some absorbent article configurations and manufacturing process conditions, increases in manufacturing speeds and/or absorbent article configuration can produce less than desirable bond strength in the material being bonded together. Thus, there is a desire for an improved energy apparatus and methods of providing energy to an item. More particularly, there is a desire for an improved ultrasonic bonding apparatus and methods of providing ultrasonic energy to an item.

SUMMARY OF THE DISCLOSURE

In one embodiment, a method of providing energy to an item may comprise positioning the item proximate an energy mechanism assembly, the energy mechanism assembly comprising: a first energy mechanism and a second energy mechanism, at least one of the first energy mechanism and the second energy mechanism comprising a planar surface and a plurality of bonding elements extending from the planar surface; and a translation system coupled to the second energy mechanism and configured to move the second energy mechanism between a first position and a second position, the translation system further configured to move the second energy mechanism along at least a first axis and a second axis between the first position and the second position. The method may further comprise positioning the item between the first energy mechanism and the second energy mechanism where the first axis is oriented substantially perpendicular to the item while the item is disposed between the first energy mechanism and the second energy mechanism and where the second axis is oriented substantially perpendicular to the first axis, moving, with the translation system, the second energy mechanism from the first position to the second position with the item disposed between the first energy mechanism and the second energy mechanism, moving, with the translation system, the second energy mechanism along the second axis for a first length while the second energy mechanism is in contact with the item, and providing, with the energy mechanism assembly, energy to the item at least while the second energy mechanism contacts the item.

In another embodiment, a method of bonding a material may comprise positioning the item proximate an energy mechanism assembly, the energy mechanism assembly comprising: a first energy mechanism and a second energy mechanism, at least one of the first energy mechanism and the second energy mechanism comprising a planar surface and a plurality of bonding elements extending from the planar surface, the plurality of bonding elements having a combined bonding surface area; and a translation system coupled to the second energy mechanism and configured to move the second energy mechanism between a first position and a second position. The method may further comprise positioning the item between the first energy mechanism and the second energy mechanism, moving, with the translation system, the second energy mechanism from the first position to the second position with the item disposed between the first energy mechanism and the second energy mechanism, and providing, with the energy mechanism assembly, energy to the item to form a plurality of bonds, wherein the plurality of bonds have a combined surface area, the combined surface area of the plurality of bonds being greater than the combined bonding surface area of the plurality of bonding elements by at least 10%.

In yet another embodiment, a bonded material may comprise a plurality of bonds, each of the plurality of bonds having a distorted shape, the plurality of bonds formed by imparting energy to the material with an energy mechanism assembly, the energy mechanism assembly comprising: a first energy mechanism and a second energy mechanism, at least one of the first energy mechanism and the second energy mechanism comprising a planar surface with a plurality of bonding elements extending from the planar surface, each of the bonding elements having a surface shape; and a translation system coupled to the second energy mechanism and configured to move the second energy mechanism between a first position and a second position, the translation system further configured to move the second energy mechanism along at least a first axis and a second axis from the first position and the second position, the second axis being perpendicular to the first axis. The distorted shape of each of the plurality of bonds is may be a distorted shape of a surface shape of one of the bonding elements.

BRIEF DESCRIPTION OF DRAWINGS

A full and enabling disclosure thereof, directed to one of ordinary skill in the art, is set forth more particularly in the remainder of the specification, which makes reference to the appended figures in which.

Repeat use of reference characters in the present specification and drawings is intended to represent the same or analogous features or elements of the disclosure.

DETAILED DESCRIPTION OF THE DISCLOSURE

Figure 1:
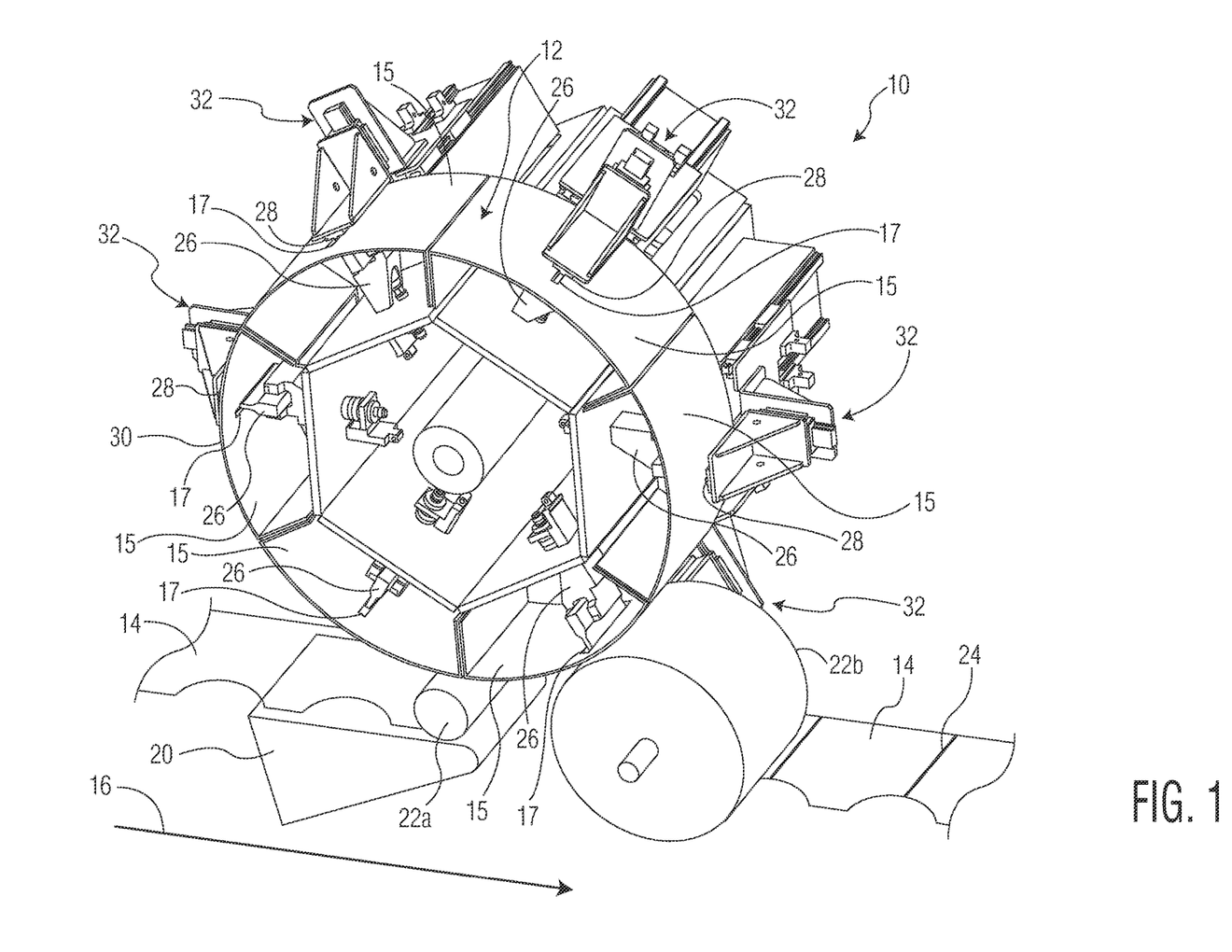
FIG. 1 is a perspective view of a preferred embodiment of an energy apparatus of the present disclosure, with some of the features of the energy apparatus being removed for purposes of clarity.

In an embodiment, the present disclosure is generally directed towards one or more energy mechanism assemblies for providing energy to an item 14. The energy mechanism assemblies may be configured to provide ultrasonic energy for ultrasonically bonding an item 14 in some embodiments. It is contemplated, however, that the described energy mechanism assemblies can provide different forms of energy to an item 14 to provide energy other than ultrasonic energy for bonding including, but not limited to, thermal energy transfer for heat sealing. In at least one preferred embodiment, the one or more energy mechanism assemblies may be implemented as part of an energy apparatus 10. The energy apparatus 10 can be utilized in various manufacturing environments and on various items. According to aspects of the present disclosure, the energy apparatus 10 herein is discussed with respect to providing an ultrasonic bond on a component of an absorbent article, such as a cross-directional pant ("CD pant"). In the embodiment of FIG. 1 and apparatus 10, the item 14 is representative of an absorbent article still in the form of a web of interconnected absorbent articles, which may be described as web 14 throughout the present disclosure. It is to be appreciated that the energy mechanism assemblies described herein and/or the larger energy apparatus 10 comprising energy mechanism assemblies can be utilized on other manufactured consumer goods, including, but not limited to, other personal care articles, specific portions of personal care articles, consumer goods, and packaging.

Each example is provided by way of explanation and is not meant as a limitation. For example, features illustrated or described as part of one embodiment or figure can be used on another embodiment or figure to yield yet another embodiment. It is intended that the present disclosure include such modifications and variations. When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. As used herein, the terminology of "first," "second," "third", etc. does not designate a specified order or that items referred to using such terms must be present sequentially, but is used as a means to differentiate between different features being described in the present disclosure. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, including, but not limited to, adult fecal incontinence garments, medical garments, surgical pads and bandages, other personal care or health care garments, and the like without departing from the scope of the present disclosure.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

Referring to FIG. 1, an energy apparatus 10 configured for providing energy to an item being transferred over a rotatable drum 12 is shown. In the embodiment described herein, the energy apparatus 10 is configured to provide ultrasonic energy to an item, such as web 14, being transferred in a machine direction 16 that is a layered assembly of various non-woven materials, film, cellulosic and superabsorbent materials, which after being cut, will form discrete absorbent articles. In some embodiments, the web 14 can include a laminate of spunbond-meltblown-spunbond ("SMS") material and elastics (e.g., strands or sheets). The web 14 can be transferred to the rotatable drum 12 and removed from the rotatable drum 12 with known web handling equipment and processes, including, but not limited to conveyors 20 and rollers 22a, 22b. In one embodiment, the energy apparatus 10 can be configured to provide an ultrasonic bond to form a side seam 24 on each side of an absorbent article, such as shown in FIG. 1. For clarity of other components of the energy apparatus 10 as described herein, the web 14 is not shown in a position over the rotatable drum 12 in FIG. 1, but only shown in an upstream position prior to engaging the rotatable drum 12 and a downstream position after disengaging from the rotatable drum 12 in FIG. 1. It should be understood that web 14 engages with drum 12 after passing roller 22a, transfers around drum 12, and disengages with drum 12 after passing roller 22b. Typically, the web 14 may be held under tension as it travels around the drum 12. Some typical tension values may be between 0.5 pounds per linear inch (PLI) (87.5 n/m) and 5 PLI (875 n/m). In the embodiment described herein, the energy apparatus 10 can form the side seam 24 on the web 14 before the web 14 is cut into discrete absorbent articles, however, it is contemplated that the energy apparatus 10 can be configured to provide energy to discrete items, such as discrete absorbent articles, as well.

The energy apparatus 10 can include a first energy mechanism 26 and a second energy mechanism 28. Together, the pair of the first energy mechanism 26 and the second energy mechanism 28 may define an energy mechanism assembly where the first energy mechanism 26 and the second energy mechanism 28 work together to impart energy to an item, such as web 14. The first energy mechanism 26 can be configured to be mounted inside of the rotatable drum 12, as shown in FIG. 1. The energy apparatus 10 can include more than one first energy mechanism 26 and more than one second energy mechanism 28. In some embodiments, the energy apparatus 10 can include two, three, four, five, six, or more pairs of first and second energy mechanisms 26, 28, providing for two, three, four, five, six, or more energy mechanism assemblies. For example, as shown in FIG. 1, the energy apparatus 10 can include six pairs of first and second energy mechanisms 26, 28. In such an embodiment, the rotatable drum 12 can be configured to include a shell 15 for each pair of first and second energy mechanisms 26, 28.

As will be described in further detail below, each shell 15 can include a slot 17 allowing for the respective first and second energy mechanisms 26, 28 to provide energy to the web 14. For discussion throughout, any reference to a single first energy mechanism 26 or a single second energy mechanism 28 is to be intended to refer to all of such energy mechanisms 26, 28 present in an embodiment, unless otherwise noted.

The first energy mechanism 26 can be configured to be fixedly coupled to the rotatable drum 12 and rotate with the rotatable drum 12. In other words, the first energy mechanism 26 can be configured to rotate with the rotatable drum 12, but remain stationary in the axial direction 27 and the radial direction 29. Although, in some embodiments, the first energy mechanism 26 may be fixedly coupled to the rotatable drum 12 but be fitted with a dampening system allowing for some movement in the radial direction 29. As depicted in FIG. 1, the first energy mechanism 26 can be disposed within at least a portion of a shell 15 of the rotatable drum 12. The second energy mechanism 28 can be configured to rotate around a circumference 30, or outer surface, of the rotatable drum 12 as will be described in more detail below. In the embodiment described herein where the energy apparatus 10 is configured to provide ultrasonic energy to the web 14, the first energy mechanism(s) 26 can be an ultrasonic horn and the second energy mechanism(s) 28 can be configured to be an anvil. Of course, it is contemplated that in an alternative embodiment the energy apparatus 10 could be configured such that the first energy mechanism 26 that is fixedly coupled to the rotatable drum 12 inside of the circumference (outer surface) 30 of the drum 12 could be an anvil and the second energy mechanism 28 that is configured to rotate around a circumference 30 of the drum 12 could be an ultrasonic horn.

Although the energy mechanism assemblies are described herein in relation to apparatus 10, comprising a rotatable drum 12, it should be understood that this is only one contemplated implementation of the described energy mechanism assemblies. Such an apparatuses 10 may be particularly suited to some high-speed manufacturing processes for forming absorbent articles, or other similar articles. However, it is contemplated that the energy mechanism assemblies described herein, including the particular coordination described between the first energy mechanism 26 and the second energy mechanism 28, may be implemented in an individual manner, separate from an apparatus 10, or even in apparatuses different than the described apparatus 10. Accordingly, any specific implementation of the energy mechanism assemblies described herein should not be construed to limit the scope of the present disclosure regarding the described the energy mechanism assemblies.

Figure 2:
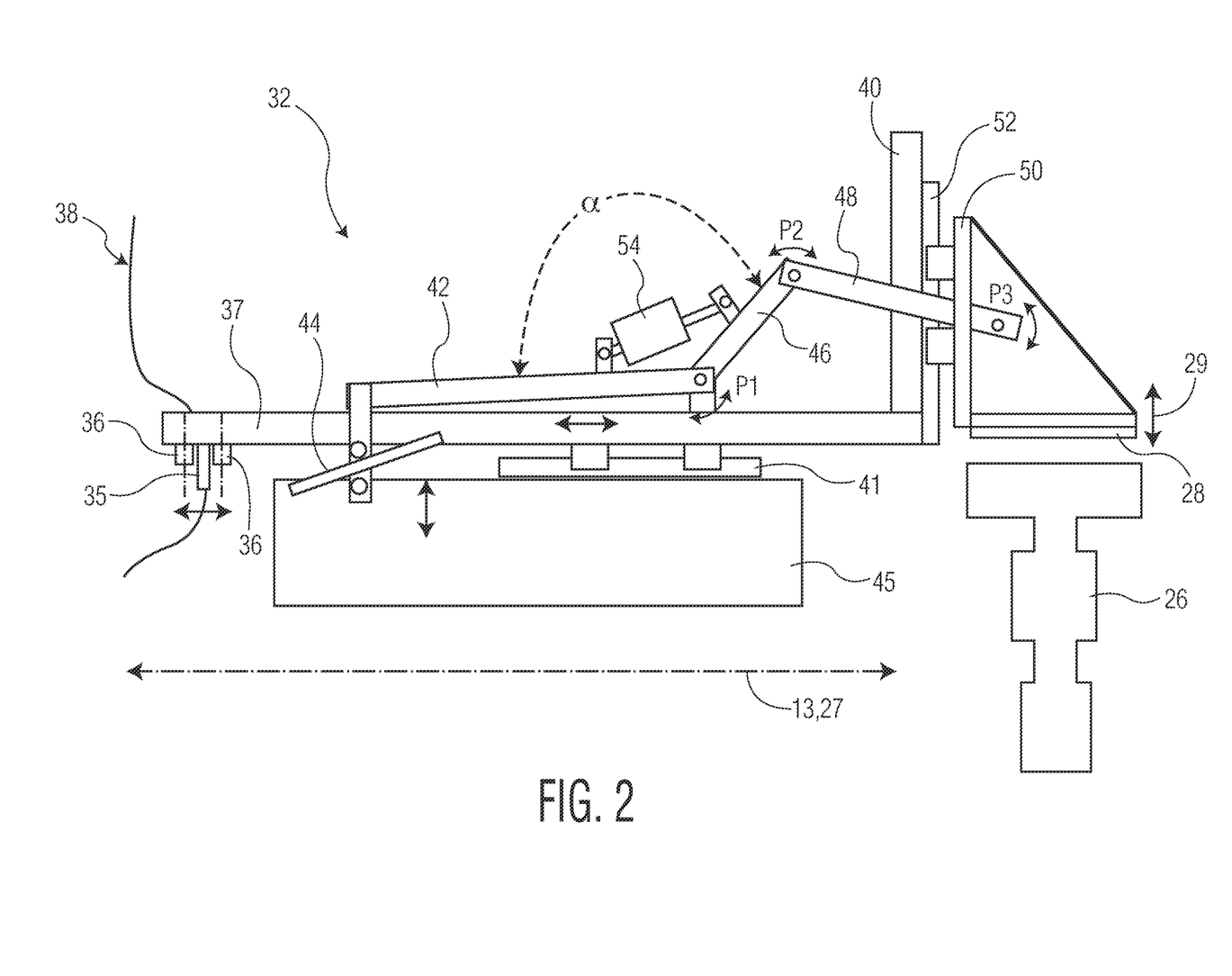
FIG. 2 is a schematic depiction of an exemplary energy mechanism assembly and translation system of the energy apparatus of FIG. 1.
Figure 3A:
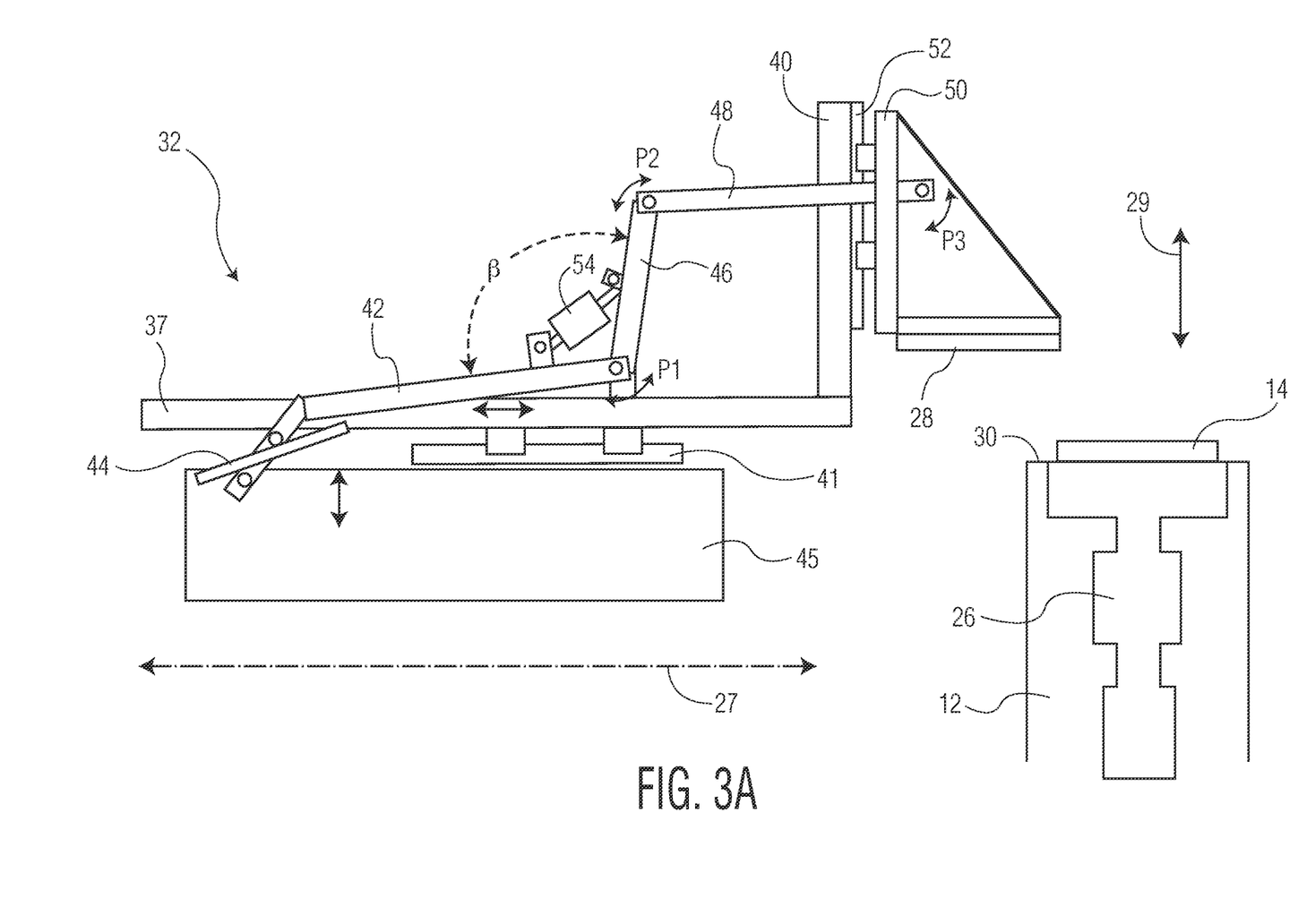
FIG. 3A is a schematic depiction of an exemplary energy mechanism assembly and translation system of the energy apparatus of FIG. 1, with the second energy mechanism in a first position.
Figure 3B:
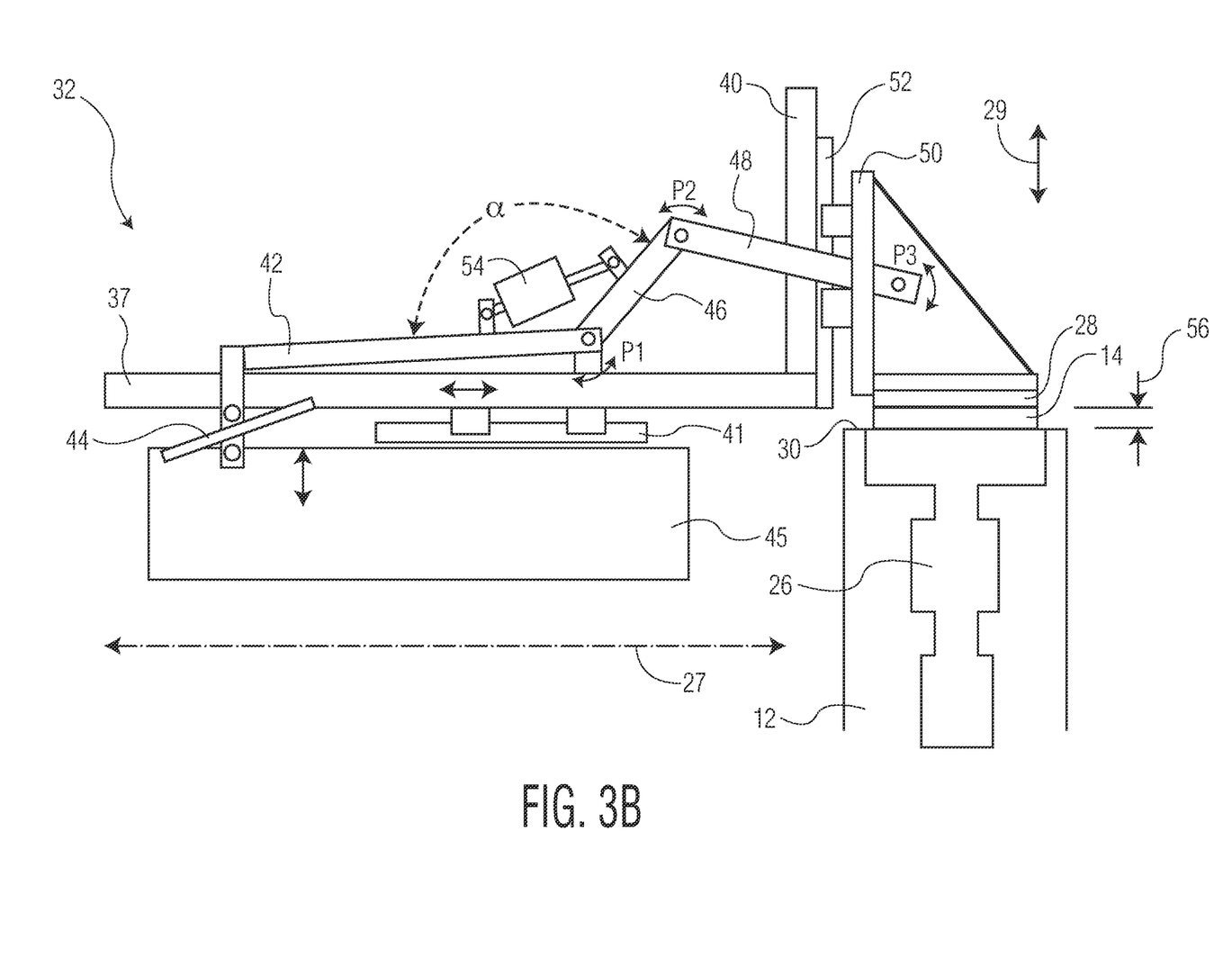
FIG. 3BA is a schematic depiction of an exemplary energy mechanism assembly and translation system of the energy apparatus of FIG. 1, with the second energy mechanism in a second position.

FIG. 2 is a schematic depiction of an energy mechanism assembly comprising a first energy mechanism 26 and a second energy mechanism 28. According to aspects of the present disclosure, the second energy mechanism 28 may be coupled to a translation system 32 operable to move the second energy mechanism 28 between a first position, for example as shown in FIG. 3A, and a second position, for example as shown in FIG. 3B. As will be described in more detail below, the translation system 32 may be configured to move the second energy mechanism 28 between the first position and the second position in both a vertical direction along a vertical axis and a horizontal direction along a horizontal axis, the horizontal axis being perpendicular to the vertical axis. As used herein, the vertical axis may be considered a first axis and the horizontal axis may be considered a second axis. When described according to the embodiment of FIG. 1 where the energy mechanism assemblies are part of apparatus 10, the horizontal direction is equivalent to the axial direction 27, extending in a direction parallel to an axis of rotation of the drum 12, and the vertical direction is equivalent to the radial direction 29, extending radially from an axis of rotation of the drum 12.

When in the first position, the second energy mechanism 28 may be generally disposed away from the first energy mechanism 26, as shown in FIG. 3A. When in the second position, the second energy mechanism 28 may be generally disposed proximate the first energy mechanism 26, as shown in FIG. 3B. According to some embodiments, the second energy mechanism 28 may be configured to be stationary in the first position and the second position for some period of time. Although, in other embodiments the second energy mechanism 28 may not be configured to spend any appreciable amount of time at the first and/or second positions. In general, the first position and the second position may define transitions in the movement of the second energy mechanism 28. For example, from the first position, the second energy mechanism 28 may begin to move toward the second position. That is, the second energy mechanism 28 may begin to move from a first position along the first axis and a first position along the second axis toward a second position along the first axis and a second position along the second axis. Conversely, from the second position, the second energy mechanism 28 may begin to move toward the first position. That is, the second energy mechanism 28 may begin to move from the second position along the first axis and the second position along the second axis toward the first position along the first axis and the first position along the second axis.

In some contemplated embodiments, the movement of the second energy mechanism 28 along the first axis and the second axis may occur at separate times. For example, the translation system 32 may be configured to first move the second energy mechanism 28 from the first position along the second axis to the second position along the second axis. Then, once the second energy mechanism 28 is at the second position along the second axis, the translation system 32 may cause the second energy mechanism 28 to move from the first position along the first axis to the second position along the first axis. Conversely, when the second energy mechanism 28 is to move from the second position to the first position, the translation system 32 may be configured to first move the second energy mechanism 28 from the second position along the first axis to the first position along the first axis. Then, once the second energy mechanism 28 is at the first position along the first axis, the translation system 32 may cause the second energy mechanism 28 to move from the second position along the second axis to the first position along the second axis.

In other contemplated embodiments, the movement of the second energy mechanism 28 between the first position and the second position may occur at least partially simultaneously. For example, the translation system 32 may be configured to move the second energy mechanism 28 between the first position along the first axis and the second position along the first axis and between the first position along the second axis and the second position along the second axis at least partially at the same time.

In some contemplated embodiments, the translation system 32 may be configured to move the second energy mechanism 28 from the first position along the first axis and the first position along the second axis toward the second position along the first axis and the second position along the second axis such that a portion of the movement occurs simultaneously. In some of these contemplated embodiments, the second energy mechanism 28 may arrive at the second position along the first axis prior to the second energy mechanism 28 arriving at the second position along the second axis. Although, in other of these contemplated embodiments, the second energy mechanism 28 may arrive at the second position along the second axis prior to the second energy mechanism 28 arriving at the second position along the first axis.

In further contemplated embodiments, the translation system 32 may be configured to move the second energy mechanism 28 from the second position along the first axis and the second position along the second axis toward the first position along the first axis and the first position along the second axis such that a portion of the movement occurs simultaneously. In some of these contemplated embodiments, the second energy mechanism 28 may begin to move from the second position along the second axis toward the first position along the second axis prior to beginning to move from second position along the first axis toward the first position along the first axis. However, at least a portion of the movement of the second energy mechanism 28 from the second position to the first position may comprise simultaneous movement of the second energy mechanism 28 from the second position along the second axis toward the first position along the second axis and from the second position along the first axis toward the first position along the first axis.

In other of these contemplated embodiments, the second energy mechanism 28 may begin to move from the second position along the first axis toward the first position along the first axis prior to beginning to move from second position along the second axis toward the first position along the second axis. In such embodiments, at least a portion of the movement of the second energy mechanism 28 from the second position to the first position may comprise simultaneous movement of the second energy mechanism 28 from the second position along the first axis toward the first position along the first axis and from the second position along the second axis toward the first position along the second axis.

In still further embodiments, the translation system 32 may be configured to move the second energy mechanism 28 between the first position and the second position such that movement of the second energy mechanism 28 begins and/or ceases simultaneously. For example, the translation system 32 may be configured to move the second energy mechanism 28 from the first position to the second position such that the second energy mechanism 28 arrives at the second position along the first axis and the second position along the second axis simultaneously. In other contemplated embodiments, the translation system 32 may be configured to move the second energy mechanism 28 from the second position to the first position such that the second energy mechanism 28 begins movement along both the first axis and the second axis simultaneously.

When in the second position, the second energy mechanism 28 and the first energy mechanism 26 are generally configured to provide energy to the web 14, thereby forming a bond pattern in the web 14. When in the second position, the second energy mechanism 28 may be configured to have an interference fit with the first energy mechanism 26. Although, in other embodiments, the second energy mechanism 28 may be configured to apply pressure against the first energy mechanism 26. In still further embodiments the second energy mechanism 28 may be configured such that there is a gap 56 between the second energy mechanism 28 and the first energy mechanism 26 when the second energy mechanism 28 is in the second position. The specifics of such spacing between the second energy mechanism 28 and the first energy mechanism 26 may be set according to a number of factors such as the amount of energy supplied to the first energy mechanism 26, the desired energy transfer to the web 14, properties of the web 14, and according to still other factors.

According to some embodiments, an energy mechanism assembly of the present disclosure may be configured to provide energy to the first energy mechanism 26 on a continuous basis such that energy may be provided to the web 14 during the entire movement of the second energy mechanism 28 in relation to the first energy mechanism 26 while the second energy mechanism 28 is proximate the first energy mechanism 26. However, in other embodiments, an energy mechanism assembly of the present disclosure may be configured to provide energy to the first energy mechanism 26 on an intermittent basis such that energy is provided to the first energy mechanism 26 while the second energy mechanism 28 is proximate the first energy mechanism 26 but not while the second energy mechanism 28 is disposed away from the first energy mechanism 26.

In any embodiment, the energy mechanism assembly and the translation system 32 may be configured such that the second energy mechanism 28 moves along the second axis for a first length 58, sometimes termed a bonding length 58 herein, while in contact with the web 14. It has been found that such movement along the second axis during bond formation results in an increased bond strength of a formed bond pattern. As described above, there are a number of different manners in which the translation system 32 may be configured to achieve such movement along the second axis—whether moving from the first position to the second position or from the second position to the first position, while in simultaneous movement along the first axis, or moving prior to, or after, movement along the first axis begins, or ceases. Although described herein as the second energy mechanism 28 moving for the bonding length 58, it should be understood that in other embodiments, the first energy mechanism 26 may configured to move for the bonding length 58. For example, once the second energy mechanism 28 is in the second position, or at least in close proximity to the second position, the first energy mechanism 26 may be configured to move for a length along the second axis, and the length of movement of the first energy mechanism 26 may be considered the bonding length 58.

It has been found that providing such motion of the second energy mechanism 28 along the second axis while the second energy mechanism 28 is in contact with the web 14 can form bond patterns having relatively increased bond strengths as compared to both a) bond patterns formed where the second energy mechanism 28 does not move along the second axis while in contact with the web 14, and b) bond patterns formed where the second energy mechanism 28 does not move along the second axis while in contact with the web 14 and for where the area of the formed bonds is equivalent. That is, forming bonds where the second energy mechanism 28 does move along the second axis during while in contact with the web 14 has been found to produce bond patterns having superior bond strengths even in comparison to those bond patterns having equivalent bonded areas but formed where the second energy mechanism 28 does not move along the second axis while in contact with the web 14. Without being bound by theory, it is believed that the movement along the second axis while in contact with the web 14 may better entangle some of the fibers of the materials comprising web 14, thereby improving its overall bond strength.

At least where the energy mechanism assemblies of the present disclosure comprise ultrasonic energy assemblies, such assemblies may be configured to bring the first energy mechanism 26 and the second energy mechanism 28 together to achieve a target force metric to form bonds while energy is supplied to the first energy mechanism 26. Such energy mechanism assemblies may additionally comprise one or more sensors, for example disposed between the first energy mechanism 26 and the second energy mechanism 28 and/or coupled to a portion of a mechanism which brings the first energy mechanism 26 and the second energy mechanism 28 together. Information from these one or more sensors may be used to determine a force metric and this determined force may be compared to a target force value. The specific target force value may be set differently under different circumstances depending on a number of factors, such as the specific energy mechanism assembly setup, the particular material comprising the web 14, the specific bond pattern to be formed, and the like. Without being bound by theory, it is believed that bond formation begins at some point after the determined force value begins rising. Although, it is also believed that bond formation begins prior to where the determined force value reaches 100% of the target force value.

Based on this understanding and theory, it is desirable for the movement of the second energy mechanism 28 along the second axis for the bonding length 58 to occur during bond formation, for example at least after the determined force value is above zero. According to some embodiments of the present disclosure, the bonding length 58 may be determined as a length of the movement of the energy mechanism 28 along the second axis while the determined force value is greater than or equal to 50% of the target force value. In embodiments where the second energy mechanism 28 moves along the second axis both in a direction toward the second position on the second and away from the second position on the second while the determined force value is greater than or equal to 50% of the target force value, the bonding length 58 may be the sum of the length of movement of the second energy mechanism 28 along the second axis both in a direction toward and away from the second position along the second axis for which the determined force value is greater than or equal to 50% of the target force value.

In embodiments where the totality of the movement along the second axis occurs while the determined force value is increasing from 50% to 100% of the target force value, or where the totality of the movement along the second axis occurs while the determined force value is decreasing from 100% to 50% of the target force value, the bonding length 58 may be between 0.75 mm and 5 mm, or more preferably between 1.5 mm and 4 mm. It is important that the bonding length 58 not be too large or this bonding method may produce apertures in the web 14 instead of bonds. It is believed that bonding lengths 58 in these embodiments may generally be less than 8 mm to prevent aperture formation rather than bond formation, or less than 7 mm in other embodiments.

In embodiments where the second energy mechanism 28 moves along the second axis both while the determined force value is increasing from 50% to 100% of the target force value (for example, when moving along the second axis toward the second position) and where the second energy mechanism 28 moves along the second axis while the determined force value is decreasing from 100% to 50% of the target force value (for example, when moving along the second axis away from the second position), the bonding length 58 may be between 1 mm and 8 mm, or more preferably between 2 mm and 6 mm. It is important that the bonding length 58 not be too large or this bonding method may produce apertures in the web 14 instead of bonds. It is believed that bonding lengths 58 in these embodiments may generally be less than 12 mm to prevent aperture formation rather than bond formation, or less than 10 mm in other embodiments.

However, in still further embodiments, the bonding length 58 may be the total amount movement of the energy mechanism 28 along the second axis while the determined force value is approximately equal to 100% of the target force value. In such embodiments, useful bonding lengths 58 may be between 0.5 mm and 4 mm, or more preferably between 1 mm and 3 mm. It is believed that bonding lengths 58 for these embodiments may generally be less than 6 mm to prevent aperture formation rather than bond formation. In one particular example according to these embodiments, a bonding length 58 of about 2.3 mm was used. A bond pattern such as pattern 65*b* shown in FIG. 6 produced by this method, and using the exemplary bonding elements 62 of FIG. 4, was found to have a bond strength approximately 7.4% greater than a bond pattern 65*a* produced by the exemplary bonding elements 62 of FIG. 4 where the bonding length 58 was zero.

Figure 4:
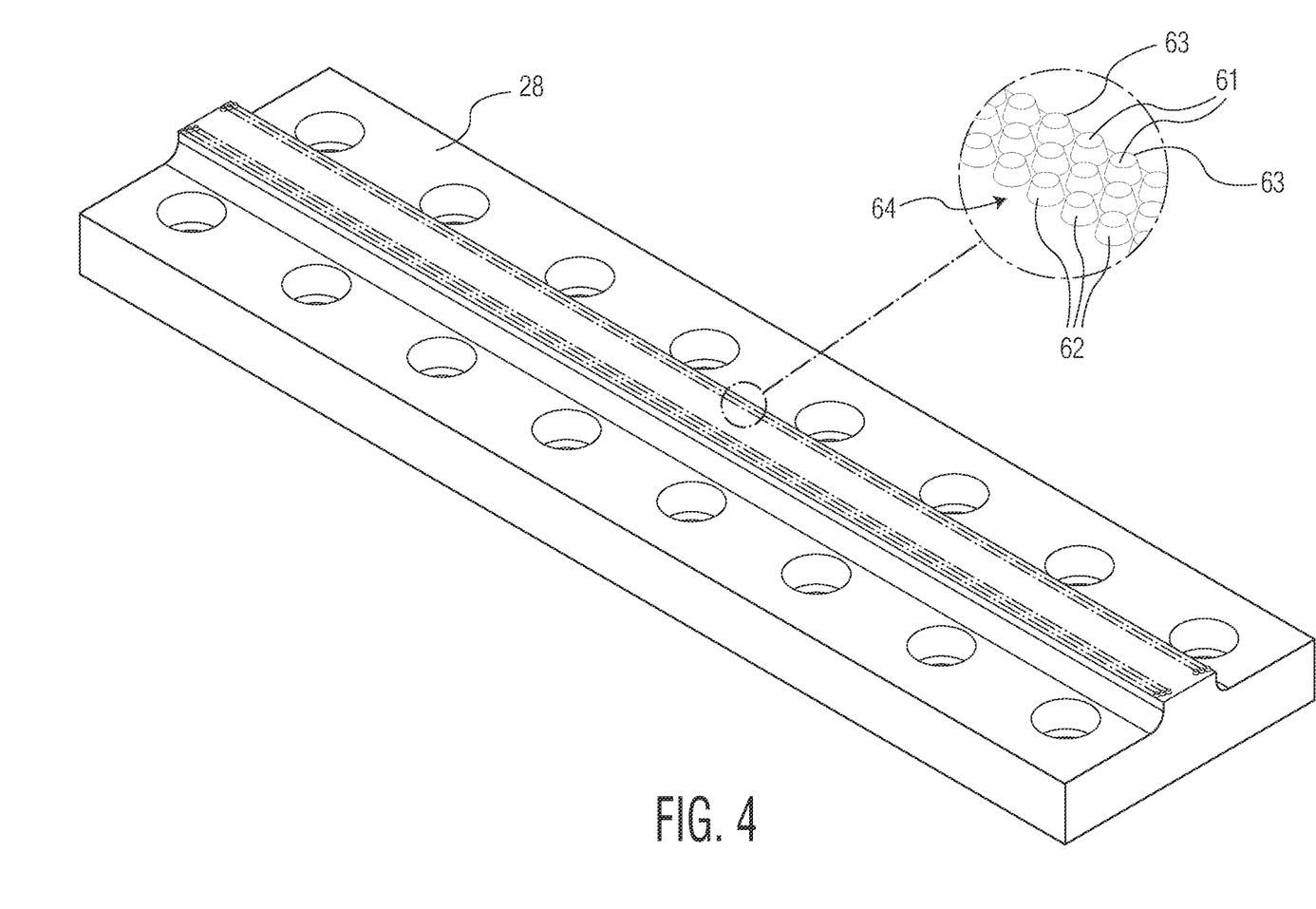
FIG. 4 is a perspective view of an exemplary second energy mechanism including bonding elements.
Figure 5:
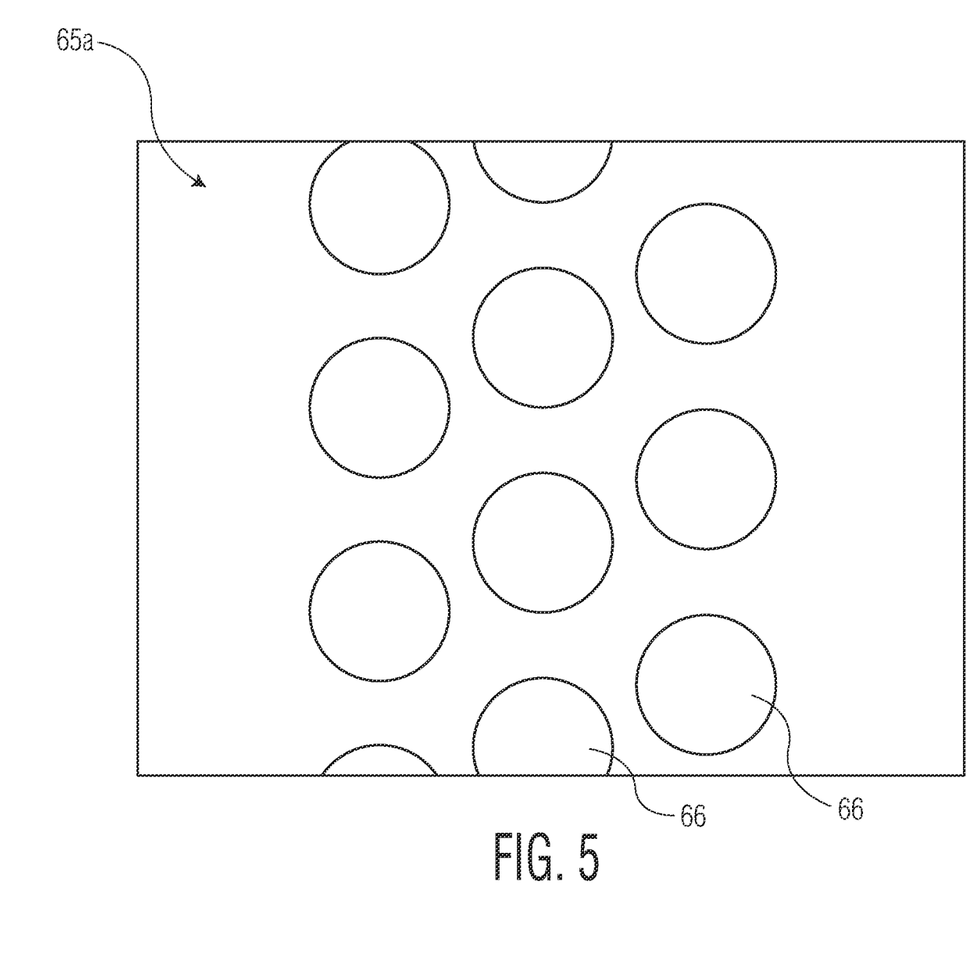
FIG. 5 is a plan view of an exemplary bond pattern, according to aspects of the present disclosure.

FIG. 4 depicts an exemplary second energy mechanism 28. Typically, the second energy mechanism 28 may comprise a relatively planar surface including a plurality of bonding elements 62 protruding from the surface, as shown in FIG. 4. Each of the bonding elements 62 generally has a surface 61 configured to face the first energy mechanism 26 while in operation, and the surfaces 61 of each of the bonding elements 62 generally defines a surface shape 63—for example formed by a perimeter of the surface 61. In the example of FIG. 4, the bonding elements 62 are shown as pins whose surfaces 61 each define a generally circular surface shape 63. Collectively, the surface shapes 63 of the bonding elements 62 define a pattern 64. The bonding elements 62 interact with the first energy mechanism 26 and, in conjunction with energy supplied by the first energy mechanism 26, form one or more bonds 66. The one or more bonds 66 collectively form a bond pattern which corresponds to the pattern 64 of the bonding elements 62, one example bond pattern being pattern 65*a* as shown in FIG. 5.

Figure 6:
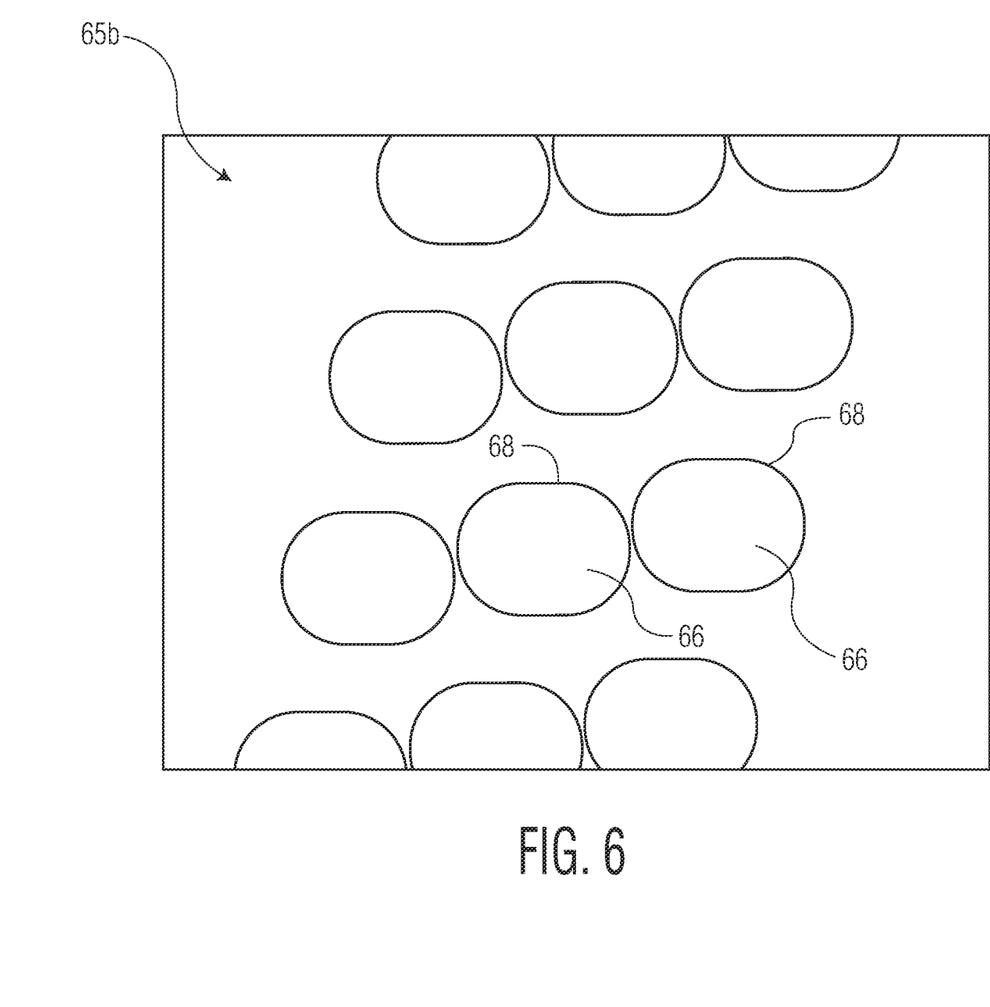
FIG. 6 is a plan view of a further exemplary bond pattern, according to aspects of the present disclosure.

According to aspects of the present disclosure, where the second energy mechanism 28 moves along the second axis for a bonding length 58 during bond formation, the movement of the second energy mechanism 28 produces bonds 66 having distorted shapes 68. FIG. 5 illustrates an exemplary bond pattern 65*a* comprising bonds 66 formed by a portion of a second energy mechanism 28 as shown in FIG. 4 used in a bonding process where the bonding length was zero. As can be seen, the shapes of the bonds 66 correspond closely to the surface shapes 63 of the bonding elements 62. By contrast, FIG. 6 illustrates an exemplary bond pattern 65*b* comprising bonds 66. Such a bond pattern 65*b* may be formed by a portion of the second energy mechanism 28 of FIG. 4 used in a bonding process where the bonding length 58 was greater than zero.

As can be seen, the bonds 66 of the bond pattern 65*b* comprise distorted shapes 68. Such distorted shapes 68 will generally correspond to the surface shapes 63 of the bonding elements 62, but will be different from the surface shapes 63. In the example of FIG. 4, where the bonding elements 62 have circular surface shapes 63, the resulting distorted shapes 68 of the pattern 65*b* may be approximately obround shapes. Although, it is not necessarily the case that the formed bonds 66 may have clearly identifiable shapes. It should be understood that the specific distorted shapes 68 of the formed bonds 66 may differ depending on the specific surface shapes 63 of the bonding elements 62 as well as how definite the bonds 66 are formed during the bonding process. Many such distorted shapes 68 may defy description by any sort of well-known shape term but are generally achieved by translating the surface shapes 63 in a plane of the web 14—for example, at least along the second axis.

It should be understood that the bonds 66 of bond pattern 65*b* have larger bond areas than corresponding surface shapes 63 of bonding elements 62 used to form the bonds 66. For example, the bonds 66 depicted in FIG. 6, which represent bonds 66 formed during a bonding process where the bonding length was about 2.3 mm and which utilized the second energy mechanism as shown in FIG. 4, can be seen having larger areas than surface areas of corresponding bonding elements 62 (of FIG. 4). The larger bond area of the bonds 66 relative to the area of the surface shapes 63 of the bonding elements 62 used to form the bonds 66 provides for a bond pattern 65*b* having greater strength than a bond pattern 65*a* formed where the bonding length 58 is zero—e.g. where there is no movement of the second energy mechanism 28 along the second axis after the second energy mechanism 28 contacts the web 14. As mentioned above, the bond strength of the bonds 66 of pattern 65*b* may also be stronger than bonds having equivalent areas to the bonds 66 but which were formed by a process where the bonding length 58 is zero. The methods described herein are additionally advantageous as larger areas of surface shapes 63 of the bonding elements 62 requires relatively more energy to be supplied to the first energy mechanism 26 to be able to form bonds 66. Accordingly, the methods of the present disclosure allow for formation of relatively larger bonds 66 at relatively lower amounts of energy supplied to the first energy mechanism 26 as well as having improved bond strengths.

The distorted shapes 68 of the bonds 66 can be considered to have a combined bonded area while the surface shapes 63 of the bonding elements 62 used to form the bonds may be considered to have a combined bonding element surface area. As is evident in FIG. 6, the combined bonded area of the distorted shapes 68 is greater than the combined bonding element surface area of the bonding elements 62. According to some aspects of the present disclosure, the described techniques can achieve examples where the combined bonded area of the distorted shapes 68 is at least 10% greater than the combined bonding element surface area of the bonding elements 62. According to further aspects of the present disclosure, the described techniques can achieve examples where the combined bonded area of the distorted shapes 68 is at least 15% greater than the combined bonding element surface area of the bonding elements 62. According to still further aspects of the present disclosure, the described techniques can achieve examples where the combined bonded area of the distorted shapes 68 is at least 20% greater, at least 30% greater, at least 40% greater, at least 50% greater, or at least 60% greater than the combined bonding element surface area of the bonding elements 62.

It should be understood that any suitable mechanism may be used to move the second energy mechanism 28 from the first position to the second position along both the first axis and the second axis, and to further move the second energy mechanism 28 for the first length 58 after contacting the web 14. In the present disclosure, FIGS. 1-3 depict one exemplary mechanism, translation system 32, for providing this particular motion of the second energy mechanism 28 which may be suitable for use in an apparatus such as apparatus 10 including a rotatable drum 12. However, this exemplary embodiment of a movement mechanism should not be construed to limit the present disclosure in any way with respect to how to achieve the particularly described motion of the second energy mechanism 28. Further details of the exemplary translation system 32 are provided below.

As best illustrated in FIGS. 2 and 3A, 3B, the translation system 32 can be configured to move the second energy mechanism 28 between a first position and a second position, for example in both the axial direction 27 and the radial direction 29. It is contemplated that the translation system 32 can be configured in various ways to move the second energy mechanism 28 in an axial direction 27 and the radial direction 29, however, one preferred embodiment is depicted in the figures herein and is described below.

In one preferred embodiment, the translation system 32 can include a first drive-side cam having a rib 35 and at least one cam follower 36, which is depicted schematically in FIG. 2. The cam follower 36 can be configured to travel a path 38 provided by the rib 35 of the first drive-side cam. As shown, a preferred embodiment includes the first drive-side cam being a rib cam, and thus, the path 38 being provided by the rib 35 that encircles the first drive-side cam. However, it is contemplated that the first drive-side cam can be in the form of other types of cams, such as, but not limited to, a barrel cam.

The translation system 32 can also include a sled 40. As shown schematically in FIG. 2, the sled 40 can be coupled to the cam follower 36 through connecting frame 37 and can be coupled to the second energy mechanism 28. The rib 35 provides a path 38 that varies in axial position depending on its circumferential position, and thus, can help provide the axial movement of the second energy mechanism 28. As shown in FIG. 2, the sled 40 can be configured to move axially along rails 41 mounted on a housing (not shown in the schematic depiction of FIG. 2).

The translation system 32 can additionally include a second drive-side cam 44 (shown schematically in FIG. 2). The translation system 32 can also include a first connecting link 42 that can be coupled to a second cam follower 45 and to the sled 40. The second cam follower 45 can follow along a path provided by the second drive-side cam 44. The translation system 32 can also include a second connecting link 46 that can be coupled to the first connecting link 42. The translation system 32 can further include a third connecting link 48 that can be coupled to the second connecting link 46 and to the second energy mechanism 28 by being coupled to a frame 50. As will be described further below, the second connecting link 46 can be configured to pivot about a first pivot point P1 and the third connecting link 48 can be configured to pivot about a second pivot point P2. The frame 50 can be configured to slide on rails 52 mounted to the sled 40 to provide for radial movement of the second energy mechanism 28.

The translation system 32 can also include an actuator 54. As depicted in FIG. 2, the actuator 54 can be coupled to the first connecting link 42 and to the second connecting link 46 and be selectively retractable to move the second energy mechanism between the first position (as shown in FIG. 3A) and the second position (as shown in FIG. 3B). When the second energy mechanism 28 is in the second position, the actuator 54 can be extended and maintain a desired angle α between the first connecting link 42 and the second connecting link 46. While moving from the second position to the first position, the actuator 54 can be actuated such that its length is shortened to pivot the second connecting link 46 about the first pivot point P1 and to pivot the third connecting link 48 about the second pivot point P2 between the second connecting link 46 and the third connecting link 48 to assist in raising the second energy mechanism 28 in the radial direction 29 to move the second energy mechanism 28 from the second position to the first position (as shown in FIG. 3A). While in the first position, the actuator 54 is retracted and maintains an angle β between the first connecting link 42 and the second connecting link 46, with angle β being less than angle α.

EMBODIMENTS

Embodiment 1: In a first embodiment, a method of providing energy to an item may comprise positioning the item proximate an energy mechanism assembly, the energy mechanism assembly comprising: a first energy mechanism and a second energy mechanism, at least one of the first energy mechanism and the second energy mechanism comprising a planar surface and a plurality of bonding elements extending from the planar surface; and a translation system coupled to the second energy mechanism and configured to move the second energy mechanism between a first position and a second position, the translation system further configured to move the second energy mechanism along at least a first axis and a second axis between the first position and the second position. The method may further comprise positioning the item between the first energy mechanism and the second energy mechanism where the first axis is oriented substantially perpendicular to the item while the item is disposed between the first energy mechanism and the second energy mechanism and where the second axis is oriented substantially perpendicular to the first axis, moving, with the translation system, the second energy mechanism from the first position to the second position with the item disposed between the first energy mechanism and the second energy mechanism, moving, with the translation system, the second energy mechanism along the second axis for a first length while the second energy mechanism is in contact with the item, and providing, with the energy mechanism assembly, energy to the item at least while the second energy mechanism contacts the item.

Embodiment 2: The method of embodiment 1, wherein the second axis may be substantially parallel with a planar surface of the item.

Embodiment 3: The method of embodiment 1 or 2, wherein the second energy mechanism has a first position along the first axis and a first position along the second axis when in the first position, and a second position along the first axis and a second position along the second axis when in the second position, and wherein the movement of the second energy mechanism along the second axis for the first length may occur after the second energy mechanism is in the second position along the first axis.

Embodiment 4: The method of any of the preceding embodiments, wherein the second energy mechanism has a first position along the first axis and a first position along the second axis when in the first position, and a second position along the first axis and a second position along the second axis when in the second position, and wherein at least a portion of the movement of the second energy mechanism along the second axis for the first length may occur while the second energy mechanism is moving from the first position along the first axis to the second position along the first axis.

Embodiment 5: The method of any one of the preceding embodiments, wherein the second energy mechanism has a first position along the first axis and a first position along the second axis when in the first position, and a second position along the first axis and a second position along the second axis when in the second position, and wherein at least a portion of the movement of the second energy mechanism along the second axis for the first length may occur while the second energy mechanism is moving from the second position along the first axis to the first position along the first axis.

Embodiment 6: The method of any one of the preceding embodiments, wherein the movement of the second energy mechanism for the first length may occur in a direction extending away from the first position along the second axis.

Embodiment 7: The method of any one of the preceding embodiments, wherein the movement of the second energy mechanism for the first length may occur in a direction extending toward from the first position along the second axis.

Embodiment 8: The method of any one of preceding embodiments may further comprise measuring an applied force on the item by the energy mechanism assembly, and wherein the first length may be determined as a sum of lengths of movement of the second energy mechanism along the second axis while the measured applied force is between 50% and 100% of a target force value.

Embodiment 9: The method of embodiment 8, wherein the first length may be between 0.75 mm and mm.

Embodiment 10: The method of any one of embodiments 1-7 may further comprise measuring an applied force on the item by the energy mechanism assembly, and wherein the first length may be determined as a sum of lengths of movement of the second energy mechanism along the second axis while the measured applied force is approximately 100% of a target force value.

Embodiment 11: The method of embodiment 10, wherein the first length may be between 0.5 mm and 4 mm.

Embodiment 12: A method of bonding a material may comprise positioning the item proximate an energy mechanism assembly, the energy mechanism assembly comprising: a first energy mechanism and a second energy mechanism, at least one of the first energy mechanism and the second energy mechanism comprising a planar surface and a plurality of bonding elements extending from the planar surface, the plurality of bonding elements having a combined bonding surface area; and a translation system coupled to the second energy mechanism and configured to move the second energy mechanism between a first position and a second position. The method may further comprise positioning the item between the first energy mechanism and the second energy mechanism, moving, with the translation system, the second energy mechanism from the first position to the second position with the item disposed between the first energy mechanism and the second energy mechanism, and providing, with the energy mechanism assembly, energy to the item to form a plurality of bonds, wherein the plurality of bonds have a combined surface area, the combined surface area of the plurality of bonds being greater than the combined bonding surface area of the plurality of bonding elements by at least 10%.

Embodiment 13: The method of embodiment 12, wherein the combined surface area of the plurality of bonds may be greater than the combined bonding surface area of the plurality of bonding elements by at least 30%.

Embodiment 14: The method of embodiment 12, wherein the combined surface area of the plurality of bonds may be greater than the combined bonding surface area of the plurality of bonding elements by at least 40%.

Embodiment 15: The method of any one of embodiments 12-14, wherein the translation system may be further configured to move the second energy mechanism along at least a first axis and a second axis from the first position and the second position, and wherein at least part of the movement along the second axis may occur while the bonding elements are in contact with the item.

Embodiment 16: The method of any one of embodiments 12-15 may further comprise measuring an applied force on the item by the energy mechanism assembly, wherein the translation system is further configured to move the second energy mechanism along at least a first axis and a second axis from the first position and the second position, and wherein at least part of the movement along the second axis may occur while the measured applied force is between 50% and 100% of a target force value Embodiment 17: The method of any one of embodiments 12-16, wherein the item may comprise at least two layers of nonwoven material and the bonds bond the at least two layers of nonwoven material together.

Embodiment 18: A bonded material may comprise a plurality of bonds, each of the plurality of bonds having a distorted shape, the plurality of bonds formed by imparting energy to the material with an energy mechanism assembly, the energy mechanism assembly comprising: a first energy mechanism and a second energy mechanism, at least one of the first energy mechanism and the second energy mechanism comprising a planar surface with a plurality of bonding elements extending from the planar surface, each of the bonding elements having a surface shape; and a translation system coupled to the second energy mechanism and configured to move the second energy mechanism between a first position and a second position, the translation system further configured to move the second energy mechanism along at least a first axis and a second axis from the first position and the second position, the second axis being perpendicular to the first axis. The distorted shape of each of the plurality of bonds may be a distorted shape of a surface shape of one of the bonding elements.

Embodiment 19: The method of embodiment 18, wherein the distorted shapes may be formed by moving the second energy mechanism along the second axis during formation of the bonds in the bonded material.

Embodiment 20: The method of embodiment 17 or 18, wherein the distorted shapes of the plurality of bonds may be a generally obround shape.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of providing energy to an item, the method comprising:

positioning the item proximate an energy mechanism assembly, the energy mechanism assembly comprising:
a first energy mechanism and a second energy mechanism, at least one of the first energy mechanism and the second energy mechanism comprising a planar surface and a plurality of bonding elements extending from the planar surface; and
a translation system coupled to the second energy mechanism and configured to move the second energy mechanism between a first position and a second position, the translation system further configured to move the second energy mechanism along at least a first axis and a second axis between the first position and the second position;
positioning the item between the first energy mechanism and the second energy mechanism where the first axis is oriented substantially perpendicular to the item while the item is disposed between the first energy mechanism and the second energy mechanism and where the second axis is oriented substantially perpendicular to the first axis;
moving, with the translation system, the second energy mechanism from the first position to the second position with the item disposed between the first energy mechanism and the second energy mechanism;
moving, with the translation system, the second energy mechanism along the second axis for a first length while the second energy mechanism is in contact with the item; and
providing, with the energy mechanism assembly, energy to the item at least while the second energy mechanism contacts the item.

2. The method of claim 1, wherein the second axis is substantially parallel with a planar surface of the item.

3. The method of claim 1, wherein the second energy mechanism has a first position along the first axis and a first position along the second axis when in the first position, and a second position along the first axis and a second position along the second axis when in the second position, and wherein the movement of the second energy mechanism along the second axis for the first length occurs after the second energy mechanism is in the second position along the first axis.

4. The method of claim 1, wherein the second energy mechanism has a first position along the first axis and a first position along the second axis when in the first position, and a second position along the first axis and a second position along the second axis when in the second position, and wherein at least a portion of the movement of the second energy mechanism along the second axis for the first length occurs while the second energy mechanism is moving from the first position along the first axis to the second position along the first axis.

5. The method of claim 1, wherein the second energy mechanism has a first position along the first axis and a first position along the second axis when in the first position, and a second position along the first axis and a second position along the second axis when in the second position, and wherein at least a portion of the movement of the second energy mechanism along the second axis for the first length occurs while the second energy mechanism is moving from the second position along the first axis to the first position along the first axis.

6. The method of claim 1, wherein the movement of the second energy mechanism for the first length occurs in a direction extending away from the first position along the second axis.

7. The method of claim 1, wherein the movement of the second energy mechanism for the first length occurs in a direction extending toward from the first position along the second axis.

8. The method of claim 1, further comprising measuring an applied force on the item by the energy mechanism assembly, and wherein the first length is determined as a sum of lengths of movement of the second energy mechanism along the second axis while the measured applied force is between 50% and 100% of a target force value.

9. The method of claim 8, wherein the first length is between 0.75 mm and 5 mm.

10. The method of claim 1, further comprising measuring an applied force on the item by the energy mechanism assembly, and wherein the first length is determined as a sum of lengths of movement of the second energy mechanism along the second axis while the measured applied force is approximately 100% of a target force value.

11. The method of claim 10, wherein the first length is between 0.5 mm and 4 mm.

12. A method of bonding a material comprising:
positioning the item proximate an energy mechanism assembly, the energy mechanism assembly comprising:
a first energy mechanism and a second energy mechanism, at least one of the first energy mechanism and the second energy mechanism comprising a planar surface and a plurality of bonding elements extending from the planar surface, the plurality of bonding elements having a combined bonding surface area; and
a translation system coupled to the second energy mechanism and configured to move the second energy mechanism between a first position and a second position;
positioning the item between the first energy mechanism and the second energy mechanism;
moving, with the translation system, the second energy mechanism from the first position to the second position with the item disposed between the first energy mechanism and the second energy mechanism; and
providing, with the energy mechanism assembly, energy to the item to form a plurality of bonds,
wherein the plurality of bonds have a combined surface area, the combined surface area of the plurality of bonds being greater than the combined bonding surface area of the plurality of bonding elements by at least 10%.

13. The method of claim 12, wherein the combined surface area of the plurality of bonds is greater than the combined bonding surface area of the plurality of bonding elements by at least 30%.

14. The method of claim 12, wherein the combined surface area of the plurality of bonds is greater than the combined bonding surface area of the plurality of bonding elements by at least 40%.

15. The method of claim 12, wherein the translation system is further configured to move the second energy mechanism along at least a first axis and a second axis from the first position and the second position, and wherein at least part of the movement along the second axis occurs while the bonding elements are in contact with the item.

16. The method of claim 12, further comprising measuring an applied force on the item by the energy mechanism assembly, wherein the translation system is further configured to move the second energy mechanism along at least a first axis and a second axis from the first position and the second position, and wherein at least part of the movement along the second axis occurs while the measured applied force is between 50% and 100% of a target force value.

17. The method of claim 12, wherein the item comprises at least two layers of nonwoven material and the bonds bond the at least two layers of nonwoven material together.

\* \* \* \* \*